United States Patent [19]

McCue

[11] 4,303,859
[45] Dec. 1, 1981

[54] INFRA-RED ANALYSIS APPARATUS AND METHOD
[75] Inventor: John McCue, Edinburgh, Scotland
[73] Assignee: Coal Industry (Patents) Limited, London, England
[21] Appl. No.: 109,243
[22] Filed: Jan. 3, 1980
[30] Foreign Application Priority Data
Jan. 9, 1979 [GB] United Kingdom ............... 00706/79
[51] Int. Cl.³ .......................... G01J 1/00; G01N 21/00
[52] U.S. Cl. ..................................... 250/338; 250/341; 250/347; 356/440
[58] Field of Search ............... 250/338, 340, 341, 347; 356/440, 51; 350/96.10
[56] References Cited
U.S. PATENT DOCUMENTS
3,460,893 8/1969 Wilks, Jr. ........................... 250/338
3,770,356 11/1973 Kimura ............................... 356/440

FOREIGN PATENT DOCUMENTS
2641176 4/1977 Fed. Rep. of Germany ...... 356/440

Primary Examiner—Davis L. Willis
Assistant Examiner—Janice A. Howell
Attorney, Agent, or Firm—Stevens, Davis, Miller & Mosher

[57] ABSTRACT

The technique of attenuated total reflection (ATR) analysis can be applied to the deposit on a filter, enabling crystalline silica deposited on a glass fibre filter to be determined, which is impossible using transmission IR spectrophotometry. An improved ATR apparatus has pressure means to bring a sample such as that collected on a filter into contact with the prism and is arranged such that the face of the prism defines the area of the sample for analysis.

7 Claims, 2 Drawing Figures

INFRA-RED ANALYSIS APPARATUS AND METHOD

This invention concerns improvements in or relating to the analysis of material, especially the analysis of material deposited on a filter, by an attenuated total reflection infra-red absorption technique, and apparatus for said technique.

The technique of attenuated total reflection (ATR), sometimes called Multiple Internal Reflection, in infra-red analysis has been known since Dr. J. Fahrenfort published details of his work in Spectrochimica Acta, 1961, 434. The technique involves passing an infra-red beam through a crystal prism, against one face of which is placed in contact a sample of the material to be analysed, so that the internally reflected beam comes into contact many times with the sample contact face of the crystal. A proportion of the beam is absorbed by the sample during its passage through the crystal before the beam leaves the crystal and is analysed. The attenuated beam gives spectra closely similar to normal transmission absorption spectra. ATR apparatus, normally including a system of four mirrors mounted on a base, with a crystal prism and prism holder, have been commercially available for some years, and may be mounted in a standard infra-red spectrophotometer. An attenuator, e.g. of the comb type, may be used in the reference beam of a double beam spectrophotometer to improve the quality of the IR spectrum obtained. In a double beam spectrophotometer, it is the difference between the IR energy levels of the sample and reference beams which is detected and plotted against the frequency of the incident radiation.

Infra-red absorption analysis has been used for many years to identify crystalline $SiO_2$ dust in the atmosphere breathed by workmen. Crystalline $SiO_2$, or alpha quartz, and other mineral dusts, can cause serious health hazards when inhaled into the lungs, and two major methods have been established in the coal mining industry to determine crystalline $SiO_2$. The first method involves filtering air and either ashing the filter or cleaning the dust from the filter, incorporating the dust in a KBr pellet then analysing by IR transmission spectroscopy for $SiO_2$. The second method is rather more straightforward and involves filtering the air on a filter which is transparent to the IR beam at the frequencies at which the quartz material is going to be analysed. A filter with deposited sample is positioned in the sample beam of a double-beam spectrophotometer, and a clean reference filter is positioned in the reference beam. The IR characteristics of the filters are essentially identical so that differences in the spectrum should be due only to the sample. Many types of synthetic filters may be used, eg. acrylonitrile or more usually PVC, but PVC filters for this method have to be exceedingly thin to minimise transmission losses and because of their fragility require support and careful handling. It would be preferable to use robust and cheap glass-fibre filters but this is not practicable for IR transmission spectroscopic analysis because of the absorption of the glass fibre itself.

It has now been found that a quantitative determination of crystalline $SiO_2$ in a dust deposit on a filter can be achieved by the ATR method. It is not yet clear to the Applicants whether no material is deposited in the interstices of the filter or whether a relatively small amount is deposited which does not affect reproducibility. An identifying IR spectrum can be obtained for the dust without interference by absorption or attenuation arising from the material of the filter.

The present invention therefore provides a method of analysing and/or quantitatively determining the deposit on a filter which comprises contacting a major face of the crystal prism of an attenuated total reflection apparatus with at least a portion of the deposit-laden face of the filter and analysing the infra-red spectrum of the deposit by attenuated total reflection.

The present invention also provides an improved IR ATR apparatus which is preferably used in the method of the invention, which apparatus comprises a crystal prism, a prism support, a beam reflection system to transmit an IR beam into and from the prism and pressure means to bring a sample surface into contact with a major face of the prism and to apply a constant pressure thereto, the arrangement being such that contact of said major face of the prism with the sample defines a constant reproducible sample area for analysis.

The invention is particularly applicable to the determination of α-quartz or cristobalite of respirable size in dust filtered from air samples, for example samples taken underground in a coal mine, or from the atmosphere of a steel foundry, and will be described in more detail for such use. The dust is preferably of a pre-determined particle size range, and conveniently a gravimetric dust sampler of the type commonly in use in the British coal mining industry is used. However, the invention may also be applied to the analysis of other dust components or pollutants or to the residue filtered from liquid suspensions. It is preferred that the filter is dry, since some liquids, such as water, can absorb or attenuate the IR beam. It is still possible to use the invention with wet filters, providing this factor is taken into account. Indeed, the apparatus of the invention may be used for ATR analysis of any desposit on a substrate.

In commercially available ATR apparatus, the prism is substantially flat, a symmetrical trapezium in plan with inclined end faces at which the IR beam enters and leaves, and two parallel major faces which form the guides for the internal reflection of the beam. One of the major faces is smaller in area than the other because of the inclination of the end faces, and this face has been invariably used as the analysing face.

Certain problems arise in applying normal ATR techniques to the analysis of a deposit on a filter. The variation of thickness of the filter itself may give problems in accurately and consistently positioning the prism, necessitating frequent recalibration of the apparatus. Furthermore, it will be appreciated that the attenuation of the IR beam by a particular substance depends not only on the quantity present on the filter but also on the area of the filter in contact with the prism face. Since filters are generally larger than the prism face, a constant area of the filter must be taken for accurate determination. This may be done by using a template and cutting out the selected area using a sharp blade. Clearly the area cannot be larger than the smaller major face as it would physically interfere with the reception of transmission of the IR beam at the end faces. For the same reason, the sample filter must be accurately positioned. It was realised that this handling of the filter could be avoided if the filter were contacted with the larger major face of the prism, the face itself serving to accurately define the area of the sample. It is preferred to use an apparatus which has means to apply a constant pressure to press the filter against the face of the prism, since this enables quantitative determination of substances to be attained.

While this may be done by a miniture torque wrench or a pendulum, a preferred embodiment of the invention uses a pneumatic or hydraulic ram which gives rapid reproducible working. Use of the ram also makes possible a self-centring device for accurate rapid positioning of the filter.

The crystal itself is conveniently thallium bromide-iodide, also called KRS-5, although other crystals may be used and may be preferred for analysing particular substances.

One embodiment of the invention will now be described by way of example only, with reference to the accompanying drawings in which.

Figure 1:
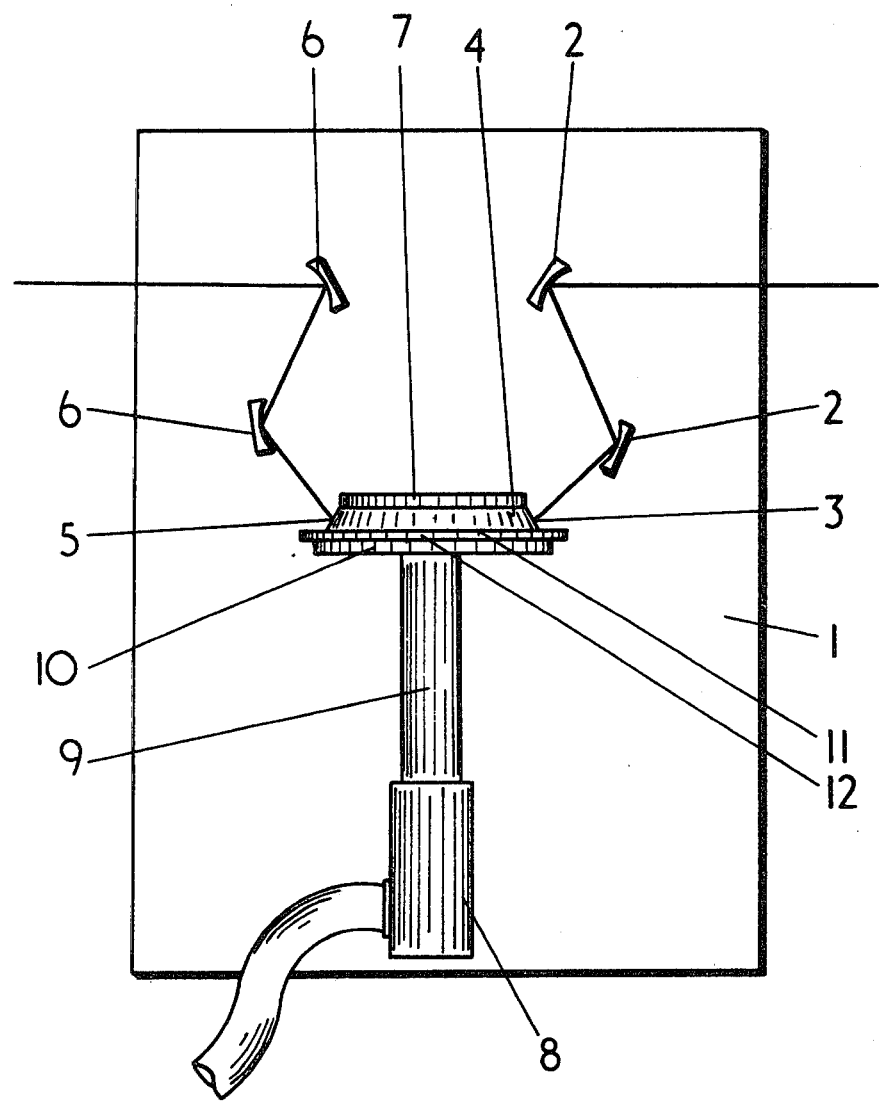
FIG. 1 shows a schematic plan view of an ATR apparatus in accordance with the invention, which is intended to be placed in the sample beam of a double beam IR spectrophotometer.

A metal base 1, carries a first pair of mirrors, 2, which are adjustable in angle to transmit an infra-red beam onto end face 3, of a thallium bromide-iodide crystal prism 4. The beam undergoes internal reflections in the prism 4, before leaving from end face 5, being transmitted via a further pair of adjustable mirrors 6, and leaving the apparatus for analysis by the detector of the IR spectrophotometer.

The prism 4 is removably positioned against a metal support plate, 7. The prism may be clamped in known manner against the support plate, or the support plate and prism may be provided with co-operating locating means. The form of such co-operating locating means is not essential to the invention and may vary, but one satisfactory form comprises the provision of two pins at right angles to the face of the support plate and upon which the bottom edge of the prism rests, and a curved wedge-shaped part is attached, e.g. by glueing, to the bottom edge of the prism so that said part fits between the pins and provides lateral location of the prism relative to the support plate.

Carefully mounted on the base 1 is a pneumatic cylinder and piston unit 8, a ram 9 being attached to the piston. Preferably, the face 10 of the ram is provided on its underside with a key (not shown) which slides within a slot (not shown) in the base 1 to ensure accurate movement of the ram relative to the crystal prism. Pressed into uniform contact with the larger major face 11 of the prism is a 55 mm diameter ready mounted glass-fibre filter 12, which is a standard filter from a gravimetric dust sampler (commercially available from Casella Ltd., England, as MRDE type 113A). The 55 mm diameter filter has an internal diameter or effective filter area, because of the metal frame or mount, of 47 mm. It was necessary to cut a commercial ATR crystal prism to avoid contact of the prism with the mount of the filter while at the same time ensuring that the maximum area of the sample deposited on the filter was subjected to analysis.

Figure 2:
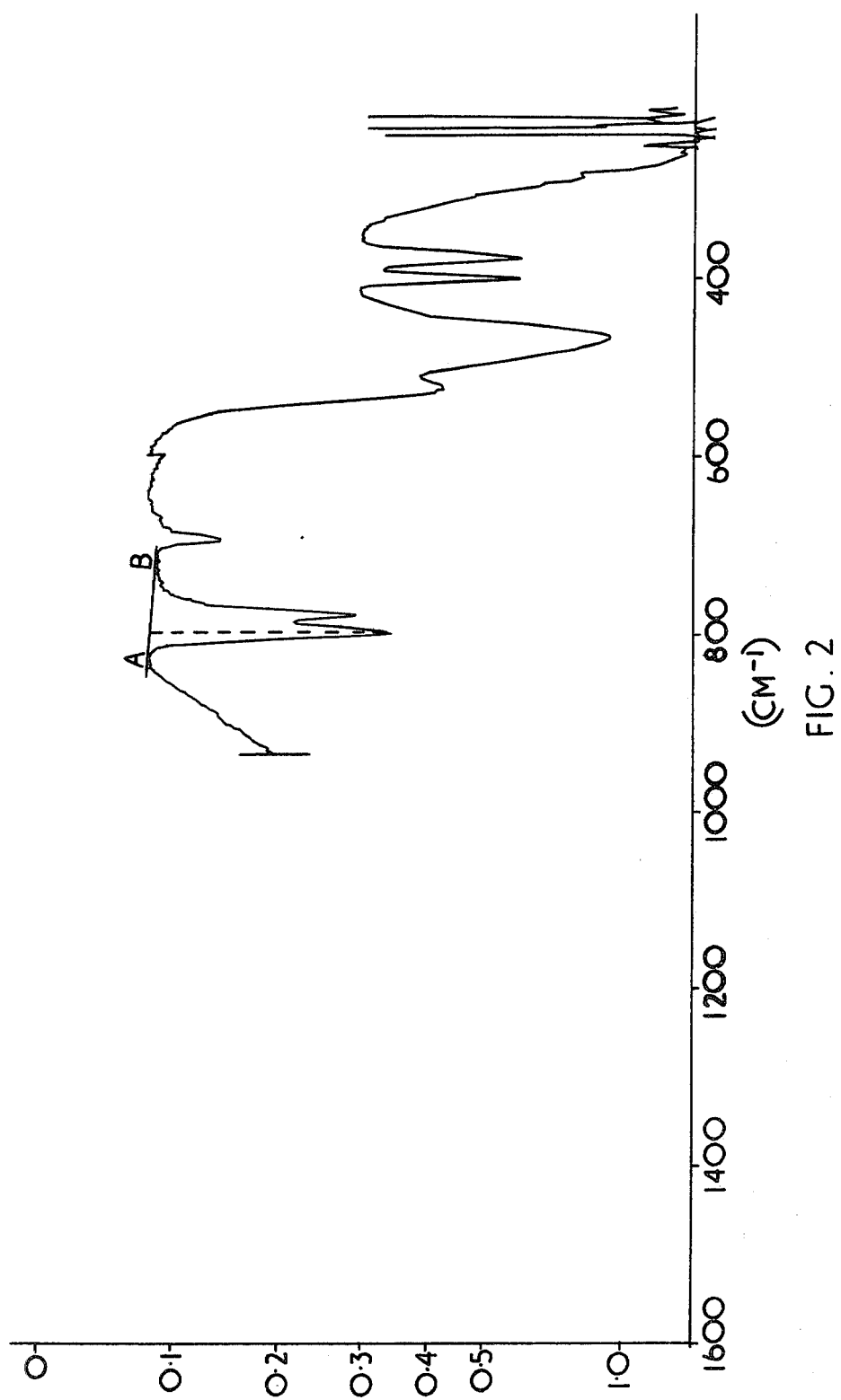
FIG. 2 shows an IR analysis using the invention.

To establish whether the method is effective, amounts of α-quartz (S.M.R.E. [Safety in Mines Research Establishment, (Sheffield)] reference No. X7488, particle size less than 5 microns) were deposited on a pre-weighed standard filters using a gravimetric dust sampler and a dust cloud chamber. The amounts deposited on the filter can be varied by varying the sampling time. The filters are removed from the sampler, reweighed, then placed in the apparatus according to the invention. The ram pushes the filter and thus the sample into contact with the prism with a pre-determined constant pressure and the apparatus placed in the sample beam of an infra-red spectrophotometer (e.g. a Perkin Elmer Model 577). If desired, to compensate for losses due to increased path length etc. an identical apparatus without the filter sample or a conventional attenuator may be placed in the reference beam. The apparatus is positioned in the beam, and the mirrors adjusted according to conventional practice for an ATR apparatus. Absorption measurements were taken at the 800 cm$^{-1}$ peak representing α-quartz; on the spectrum obtained, a tangential base line is drawn from minimum absorption prior to 800 cm$^{-1}$ to minimum absorption after the quartz peak at 780 cm$^{-1}$. The vertical line from the peak at 800 cm$^{-1}$ to the base line represents the absorption due to quartz (see FIG. 2). It was discovered that there was an essentially linear relationship between absorbance and weight of quartz and that a high absorption to weight ratio is achieved in the method of the invention.

On completion of the analysis the ram is retracted, for example the pneumatic pressure may be by-passed and the ram retracted with the aid of a spring or manually. The filter is removed and the crystal prism is lifted out for cleaning before being repositioned for the next analysis.

The apparatus as described above offers reproducible quantitative analyses of crystalline silica in air-borne dust while at the same time minimising time-consuming manual work. Minimised handling is itself also likely to contribute to accuracy of results.

The apparatus as described may, of course, be varied without departing from the scope of the invention. Conveniently, the position of the support plate for the crystal prism can be adjusted, e.g. by a lockable screw arrangement, to enable the apparatus to be calibrated, no adjustment after calibration should be necessary. Calibration, and the alteration of the angle of incidence of the IR beam, which determines the number of internal reflections within the crystal prism, are conventional practice in the ATR art.

A convenient form of the apparatus is one in which the base 1 is hingedly attached to a base plate which can itself be secured, e.g. by screws, into the IR spectrophotometer. Tilting of the base relative to the base plate facilitates positioning of the crystal prism and positioning of the filter. Preferably, the edge of the filter is placed in a slot in an extension of the support plate, which holds the filter adequately in position before actuation of the ram, and acts as a self-centring device.

Since the method is not limited by the material of the filter as in standard IR transmission spectrophotometry, it is possible to scan over the useful range of 4000 cm$^{-1}$ to 200 cm$^{-1}$ and this increased range provides access to useful and often important information concerning other contaminants present in samples.

I claim:

1. An IR attenuated total reflection apparatus capable of reproducible quantitative analysis of crystalline silica in air-borne dust, said apparatus comprising a planar crystal ATR prism having a smaller major face and a larger major face and edges, one pair of edges being bevelled and capable of acting as entry and exit faces for an IR beam, a prism support, a beam reflection system for transmitting an IR beam into and from the edges of said prism, and pressure means for bringing a planar sample into contact with the larger major face of the prism and for applying a constant reproducible predetermined pressure thereto, the contact of said larger major face of the prism with the sample defining a constant reproducible sample area for analysis.

2. An apparatus according to claim 1, wherein the pressure means comprises a hydraulic or pneumatic ram.

3. An apparatus according to claim 1, wherein the prism and the prism support are provided with co-operating location means whereby the prism may be removably accurately positioned.

4. An apparatus according to claim 1, comprising also a self-centring device to facilitate positioning of the sample relative to the prism.

5. A method of quantitatively analyzing a material deposited on a filter which comprises the steps of providing a crystal ATR prism having a smaller major face and a larger major face, contacting the larger major face of said ATR prism with at least a portion of a deposit-laden face of a filter to define a constant reproducible area for analysis, said contact being at a constant reproducible predetermined pressure, passing an IR beam through said prism and analyzing the infra-red spectrum of the deposit by attenuated total reflection of the IR beam passing through said prism.

6. A method according to claim 5, wherein a hydraulic or pneumatic ram is used to contact the filter with the larger major face of the prism at a constant predetermined pressure.

7. A method according to claim 5, wherein the filter is a glass-fibre filter.

* * * * *